United States Patent [19]

Pollard, Jr.

[11] 4,260,681
[45] Apr. 7, 1981

[54] REAGENT SYSTEM AND METHOD FOR ASSAYING PEPTIDASE ENZYMES

[75] Inventor: John K. Pollard, Jr., La Jolla, Calif.

[73] Assignee: Calbiochem-Behring Corp., La Jolla, Calif.

[21] Appl. No.: 973,851

[22] Filed: Dec. 28, 1978

[51] Int. Cl.³ .......................... C12Q 1/32; C12Q 1/36
[52] U.S. Cl. .......................................... 435/24; 435/26
[58] Field of Search ................... 435/24, 26; 195/103.5 R, 99; 260/112.5 R

[56] References Cited

U.S. PATENT DOCUMENTS

| | | | |
|---|---|---|---|
| 3,591,459 | 7/1971 | Haschen et al. | 435/24 |
| 3,862,011 | 1/1975 | Smith | 435/24 |
| 3,925,162 | 12/1975 | Kanno | 435/24 X |
| 4,006,061 | 2/1977 | Weeks et al. | 435/26 |
| 4,116,774 | 9/1978 | Minato et al. | 435/24 |

OTHER PUBLICATIONS

Kojima et al., *Clinica Chimica Acta*, 93 (1979) 181–187.
Patchornik et al., *JACS*, 86, 1206 (1964).
Shifrin et al., *J. Biol. Chem.*, 234, 1555 (1959).
Doherty et al., *J. Biol. Chem.*, 147, 617 (1943).
Bergmeyer, *Methods of Enzymatic Analysis*, Academic Press, New York, 949–954 (1974).

*Primary Examiner*—Esther M. Kepplinger
*Attorney, Agent, or Firm*—Natalie Jensen

[57] ABSTRACT

A reagent system for assaying a biological specimen for a peptidase enzyme comprising a peptide substrate in which the C-terminal amino acid is dehydroalanine, the enzyme lactate dehydrogenase, the reduced coenzyme nicotinamide adenine dinucleotide and a buffer material.

14 Claims, No Drawings

REAGENT SYSTEM AND METHOD FOR ASSAYING PEPTIDASE ENZYMES

SUMMARY OF THE INVENTION

The present invention relates to a reagent system and method for assaying a biological specimen for a peptidase enzyme. The invention also relates to certain novel dehydroalanine peptides which are employed as substrates in the instant invention.

The determination of peptidase enzymes is becoming increasingly important in clinical biochemistry where the enzyme levels are of significant diagnostic value. For example, the determination of cystine aminopeptidase is a valuable guide in the management of complicated pregnancies. Moreover, the determination of dipeptidyl aminopeptidase II (DAP II) as well as dipeptidyl aminopeptidase IV (DAP IV) is of value in the diagnosis of muscle diseases. Specifically, significant increases in DAP II have been observed in patients with muscular dystrophies and polymyositis whereas DAP IV shows a marked increase in a variety of muscle wasting conditions. Lowered serum levels of DAP IV have been observed in patients with blood cancers (i.e., acute lymphatic leukemia, lymphosarcoma, Hodgkins disease) as well as gastric cancers. The determination of leucine aminopeptidase (LAP) is employed in the differential diagnosis of jaundice, particularly in intra and extrahepatic obstructive jaundice. Raised values of LAP are found in acute hepatitis, in pancreatitis, and pregnancy. The determination of renal dipeptidase appears to have some significance in the diagnosis of renal impairment.

In the instant invention, the determination of peptidase enzymes is accomplished by utilizing the ability of the enzymes to convert dehydroalanine peptides to dehydroalanine. The latter compound decomposes spontaneously to yield pyruvate which is converted to lactate by lactate dehydrogenase (LDH) with the simultaneous conversion of reduced nicotinamide adenine dinucleotide (NADH) to its oxidized form (NAD). The rate of formation of NAD is measured photometrically and is proportional to the peptidase activity of the sample.

Accordingly, a first aspect of the present invention relates to a reagent system for assaying a biological specimen for a peptidase enzyme which system comprises a peptide substrate in which the C-terminal amino acid is dehydroalanine, the enzyme lactate dehydrogenase, the reduced coenzyme nicotinamide adenine dinucleotide and a buffer material.

Another aspect of the present invention relates to a method of assaying a biological specimen for a peptidase enzyme which method comprises dissolving the reagent system of the invention in water to obtain liquid reagent; mixing the liquid reagent with the specimen whereby the dehydroalanine peptide substrate is hydrolyzed to produce pyruvic acid which oxidizes NADH to NAD; and determining the concentration of NAD with time.

Still another aspect of the present invention relates to certain novel dehydroalanine peptide substrates, namely,
L-leucyl-dehydroalanine,
glycyl-L-prolyl-dehydroalanine,
L-lysyl-L-alanyl-dehydroalanine, and
S-benzyl-L-cysteinyl-dehydroalanine and the use of these substrates in the instant invention.

DETAILED DESCRIPTION OF THE INVENTION

The dehydroalanine peptide substrates employed in the instant invention are prepared according to the following reaction sequence:

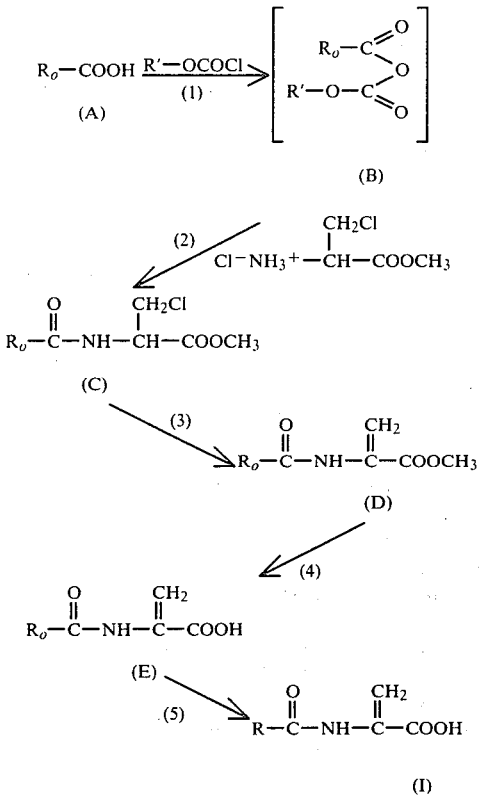

wherein $R_o$COOH is an amino acid or peptide in which the amino carboxy and/or thiol functions in the $R_o$ group are suitably protected; $R=R_o$ minus the amino and/or carboxy protecting groups; and R' is lower alkyl of 1 to 4 carbon atoms.

Step 1 of the process is effected by treating a suitably protected amino acid or peptide of formula (A) with a lower alkyl chloroformate in an organic solvent in the presence of a tertiary amine. Typically this treatment is conducted at temperatures in the range of $-10°$ to $-20°$ C. for about from 3 to 7 minutes. Suitable solvents which can be used include tetrahydrofuran, dimethoxyethane, dimethylformamide and the like. Tetrahydrofuran is preferred. Tertiary amines that can be used include triethylamine, N-methylmorpholine, diisopropylethylamine and the like. The resulting anhydride product of formula (B) is not isolated but used directly in the next step.

Step 2 is effected by treating the anhydride obtained in Step 1 with β-chloroalanine methyl ester hydrochloride in the presence of a tertiary amine such as those previously mentioned. Typically, the reaction is conducted at temperatures in the range of $-10°$ to $20°$ C. for about from 20 minutes to 1.3 hours. The resulting product (C) is separated by conventional procedures.

Step 3 is effected by treating the β-chloroalanine methyl ester derivative of formula (C) with a tertiary amine, or hindered secondary amine, in an organic solvent. Typically, the reaction is conducted at room temperature for about from 30 minutes to 1.3 hours. Tertiary and hindered secondary amines that can be used include triethylamine, dicyclohexylamine, N-ethylpiperidine and the like. Solvents which can be used include ethyl acetate, chloroform and methylene chloride.

Step 4 is effected by treating the dehydroalanine methyl ester derivative of formula (D) with an inorganic base. Typcially, treatment of the ester is carried out in a lower alkanol (e.g. methanol, ethanol, etc.) at room temperature for about from 40 minutes to 3 hours. Inorganic bases that can be employed include alkali hydroxides such as sodium hydroxide and potassium hydroxide.

Step 5, directed to deprotection of the amino function(s) in compounds of formula (E), can be effected by conventional procedures used in the art. For example, tert-butoxycarbonyl protecting groups can be cleaved by treatment with trifluoroacetic acid at room temperature for about from 20 minutes to one hour. The resulting product, a trifluroracetate salt, is subjected to anion-exchange and then lyophilized to afford the corresponding salt or zwitterion of formula (I).

Starting materials required in the foregoing reaction sequence (i.e., compounds of the formula $R_oCOOH$ wherein $R_oCOOH$ represents an amino acid or peptide in which the amino or thiol functions in the $R_o$ group are suitably protected) are either available or can be obtained by known processes.

For example, protection of the amino function can be accomplished via acylation with tert-butyloxycarbonyl azide to yield the corresponding tert-butoxycarbonyl protected amino derivative. A thiol function can be protected via benzylation with benzyl chloride.

The dehydroalanine peptide substrates (I) are employed in the quantitative measurement of peptidase enzymes in the instant invention as depicted below:

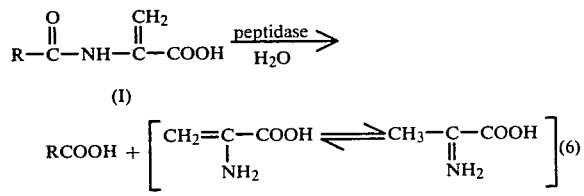

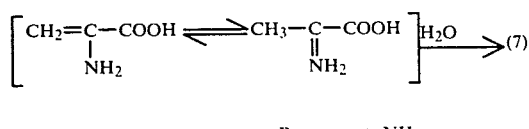

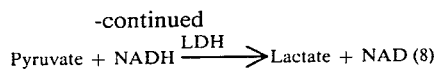

wherein NADH and NAD are reduced and oxidized nicotinamide adenine dinucleotide respectively and LDH is lactate dehydrogenase.

As depicted above, a dehydroalanine peptide substrate (I) undergoes hydrolysis in the presence of a peptidase to yield an amino acid or peptide (i.e., RCOOH), pyruvate and ammonia. The hydrolysis occurs in two consecutive steps, the first being enzymatic (6) and the second being spontaneous (7). The pyruvate liberated by the spontaneous hydrolysis of dehydroalanine is converted to lactate in the presence of lactate dehydrogenase with the simultaneous conversion of NADH to NAD (8). Since NADH absorbs light very strongly at 340 nm, while NAD does not, the rate at which NAD is formed is directly proportional to the decrease in absorbance of light at 340 nm, constant temperature, usually 20° to 40° C., and constant pH. This decrease in absorbance is readily measured using a conventional UV spectrophotometer. Since the rate of formation of NAD is proportional to the rate at which pyruvate is consumed, the decrease in absorbance gives a direct measure of the original concentration of piptidase in the biological specimen.

As mentioned previously the reagent system of the invention comprises a peptide substrate in which the C-terminal amino acid is dehydroalanine, the enzyme lactate dehydrogenase (LDH), the reduced coenzyme nicotinamide adenine dinucleotide (NADH) and a buffer material. Enzyme activators, stabilizers and bulking agents may also be included.

Preparation of the reagent system is most advantageously effected by combining:

(1) a homogeneous blend of substrate, lyophilized LDH, buffer material and, optionally, enzyme activators and/or stabilizers; and (2) NADH just prior to use.

The substrate employed in the reagent system will depend on the specific peptidase to be assayed. The following table summarizes appropriate dehydroalanine peptide substrates as well as assay conditions, (i.e., optimum pH, activators and inhibitors), where known, for specific peptidase enzymes that can be assayed according to the instant invention.

| Enzyme | Substrate | Ph Optimum | Activators | Inhibitors |
|---|---|---|---|---|
| renal dipeptidase | glycyl-dehydroalanine L-alanyl-dehydroalanine | 7.5 | $Zn^{2+}$ | Inorganic phosphate, nucleotides, monovalent anions ($HCO_3-$, $OAc^-$, $Cl^-$) |
| leucine aminopeptidase | L-leucyl-dehydroalanine | 9.0 | $Mg^{2+}$, $Mn^{2+}$ | $Cd^{2+}$, $Cu^{2+}$, $Hg^{2+}$ $Pb^{2+}$, alcohols |
| dipeptidyl aminopeptidase II | L-lysyl-L-alanyl-dehydroalanine | 4.5–5.5 | None | Cations: puromycin$^+$, Tris$^+$, Na$^+$ |
| dipeptidyl aminopeptidase IV | glycyl-L-prolyl-dehydroalanine | 7.6–7.8 | None | $Pb^{2+}$, $Hg^{2+}$, $Zn^{2+}$ |
| cystine aminopeptidase | S-benzyl-L-cysteinyl-dehydroalanine | 6.0–7.0 | | |

The particular buffer material employed in the reagent system will depend on the assay reaction to be conducted. Normally, the buffers employed will be zwitterionic buffers, such as, for example, TES (N-tris(-hydroxymethyl)methyl-2-aminoethanesulfonic acid)

and the salts thereof. Exemplary of other switterionic buffers which may also be satisfactory are CAPS [-(N-morpholino) propane sulfonic acid], TAPS [N-tris-(hydroxymethyl0methyl-3-aminopropanesulfonic acid] HEPES[N-2-hydroxyethylpiperazine-N'-2-ethanesulfonic acid], MES[2-N-morpholino-ethanesulfonic acid] and the like and the salts thereof. The use of organic amine buffers is also feasible in certain instances. For example, a combination of TRIS [tris(hydroxymethyl)aminomethane] and TES can be used in the reagent system employed in assaying renal dipeptidase, however, TRIS is not suitable as a buffer material in the reagent system employed in assaying dipeptidyl aminopeptidase II.

In the present invention it is necessary that the amount of peptidase enzyme be rate limiting. Accordingly, individual components in the reagent system should be present in amounts suitable to ensure that the observed reaction rate for the assay system is characteristic of and determined by the rate of the pipetidase catalyzed reaction (reaction 6).

The method of assaying a biological specimen for a specific peptidase enzyme according to the present invention comprises dissolving the appropriate reagent system in water to obtain a liquid reagent; mixing the liquid reagent with the biological specimen whereby the substrate is hydrolyzed to yield pyruvate which oxidizes NADH to NAD; and measuring the rate of formation NAD.

The term "biological specimen" as used herein refers to body fluids such as serum, plasma and urine.

DESCRIPTION OF SPECIFIC EMBODIMENTS

The following specific description is given to enable those skilled in the art of more clearly understand and practice the present invention. It should not be considered as a limitation upon the scope of the invention but merely as being illustrative and representative thereof.

PREPARATION A

To a stirred suspension of 104 g of phosphorous pentachloride in 550 ml of methylene chloride at $-10°$ C., is added 70 g of L-serine methyl ester hydrochloride, in approximately 5 g portions, over a period of 40 minutes while the temperature is maintained between $-10$ and $0°$ C. The reaction mixture is then allowed to warm to room temperature with stirring. Stirring is continued for 2-3 hours and the mixture is then poured into 550 ml of stirred petroleum ether. The resultant mixture is filtered and the filter cake is washed with petroleum ether ($3 \times 100$ ml) and then with ether ($2 \times 100$ ml). The combined filtrate and washings are dried under vacuum over sodium hydroxide pellets to afford 71 g of $\beta$-chloroalanine methyl ester hydrochloride.

PREPARATION B

L-proline methyl ester hydrochloride (16.6 g, 100 mmoles dissolved in 100 ml methylene chloride is treated with 14 ml (100 mmoles) of triethylamine. The precipitate which forms is removed by filtration and the filtrate is then added to 17.5 g (100 mmoles) tert-butyloxycarbonyl glycine in 150 ml methylene chloride. The resultant solution is cooled to $-5°$ C. and 23 g (112 mmoles) of dicylohexylcarbodiimide dissolved in 25 ml of methylene chloride is added with stirring. The reaction mixture is stirred at $-5°$ to $0°$ C. for approximately 90 minutes and then overnight at room temperature. A few drops of acetic acid are added to destroy excess carbodiimide and the cicyclohexyl urea precipitate is then removed from the reaction mixture by filtration. The filtrate is evaporated to afford an oily residue which is redissolved in 100 ml ethyl acetate. The resultant solution is filtered and the filtrate extracted successively with 1 M sodium carbonate/saturated sodium chloride (30:70) 1 M citric acid and saturated sodium chloride. The organic layer is separated, dried over magnesium sulfate, filtered and evaporated to afford an oil which is crystallized from ether/petroleum ether. The crystalline material is characterized using thin-layer chromatography on silica gel developed with $CHCl_3/CH_3OH/CH_3CO_2H$ (10:2:1). The product, tert-butyloxycarbonyl-glycine-L-proline methyl ester, obtained in 50% yield exhibits an Rf of 0.75, m.p. 66°–67° C.

The above obtained ester (16.9 g, 59 mmoles) dissolved in 60 ml of methanol is treated with 73 ml of 1 M sodium hydroxide. After 1 ½ hours at room temperature, methanol is removed by evaporation. The reaction mixture is then filtered, cooled to 10° C. and acidified with solid citric acid to pH3. The resultant solution is extracted with ethyl acetate and the extract is then washed with a saturated sodium chloride solution. The organic phase is separated and dried over magnesium sulfact. After drying, the solution is filtered and evaporated to afford a crystalline material which is characterized using thin layer chromatography on silica gel developed with $CHCl_3/CH_3OH/CH_3CO_2H$ (10:2:1). The product, tert-butyloxycarbonyl-glycyl-L-proline, obtained in 49% yield exhibits an Rf of 0.60, m.p. 140°–143° C.

PREPARATION C

To a suspension of 31 g (122 mmoles) of L-lysine hydrochloride in 240 ml of dimethylsulfoxide is added 49.4 g (488 mmoles) of triethylamine and 36.8 g (257 mmoles) of tert-butyloxycarbonylazide. The suspension is stirred at room temperature for 3 days and then poured into 1.2 liters of chilled water. The pH of the resultant solution is adjusted to 9.4 with 1 M NaOH and then extracted with ether. The aqueous phase is acidified to pH 3.3 with solid citric acid and then extracted with ethyl acetate. The ethyl acetate extract is washed with water and then dried over anhydrous magnesium sulfate. After drying, the extract is filtered and the filtrate is then evaporated under reduced pressure to afford an oil. The oil is triturated with petroleum either to obtain a gum which is dried under vacuum to yield an amorphous solid. The solid is characteriszed using thin-layer chromatography on silica gel developed with $CHCl_3/CH_3OH/CH_3CO_2H$ (10:2:1). The product, bis-tert-butyloxycarbonyl-L-lysine, obtained in 40% yield exhibits and Rf of 0.65.

Bis-tert-butyloxycarbonyl-L-lysine (17 g, 49 mmoles) and 7 g (60.8 mmoles) N-hydroxysuccinimide are dissolved in 165 ml of tetrahydrofuran. The solution is then cooled to $-2°$ C. and 10.3 g (50 mmoles) of dicyclohexylcarbodiimide is added. The reaction mixture is stirred at 0° C. for 2 hours and then refrigerated. After over-night refrigeration, several drops of acetic acid are added and the reaction mixture is again refrigerated for approximately 30 minutes. Thereafter, the mixture is filtered and the collected solid material washed with tetrahydrofuran. The combined filtrate and washings are then evaporated under reduced pressure to afford an oil. The oil is diluted with 100 ml of ether and the precipitate present is removed by filtration. The filtrate is then diluted with 400 ml ether to obtain a turbid solution. Refrigeration of the solution produces 8.53 g of crystalline material. An additional 4.75 g of material is obtained from the mother liquor upon further dilution with ether followed by refrigeration. The combined material is recrystallized and then characterized using thin-layer chromatography on silica gel developed with $CHCl_3/CH_3OH/CH_3CO_2H$ (10:2:1). The product, bis-tert-butyloxycarbonyl-L-lysine-N-hydroxysuccinimide ester, obtained in 42% yield exhibits an Rf of 0.80.

L-Alanine (2.8 g, 31.4 mmoles) and 3.14 g (31.4 mmoles) of potassium bicarbonate are dissolved in 30 ml of water and the solution is cooled to 2° C. Thereafter, 9.3 g (20.9 mmoles) of bis-tert-butyloxycarbonyl-L-lysine-N-hydroxysuccinimide ester in 30 ml of acetonitrile is added to the solution dropwise with vigorous stirring. An additional 10 ml of acetonitrile is then added to redissolve the precipitated ester. After 1 hour at 20° C. the reaction mixture is allowed to warm to room temperature and stirring is continued overnight. The resulting biphasic solution is dried under reduced pressure to remove acetonitrile and then acidified with solid citric acid to pH 2.5. The oil which separates is extracted with ethyl acetate and the extract is then washed with water and dried over magnesium sulfate. After drying, the product is filtered and dried under reduced pressure to afford an oil residue. Trituration of the oil with warm benzene yields a semisolid mass. The solid material is transferred to a filter, pressed to a cake and washed with petroleum ether to afford a powder which is dried under vacuum. The powdery material is characterized using thin layer chromatography on silica gel developed with $CHCl_3/CH_3OH/CH_3CO_2H$ (10:2:1). The product, bis-tert-butyloxycarbonyl-L-lysyl-L-alanine, obtained in 67% yield, exhibits an Rf of 0.67.

EXAMPLE I

To a solution of 87.1 g (350 mmoles) t-butyloxycarbonyl-L-leucine hydrate in 500 ml of ethyl acetate is added 42 g of anhydrous magnesium sulfate. The mixture is stirred at room temperature for 5 hours, then filtered and the solid material collected and washed with ethyl acetate. The filtrate and washings are combined and dried under reduced pressure to afford t-butyloxycarbonyl-L-leucine as an oil.

The above obtained oil is dissolved in 1.4 liters of tetrahydrofuran and 48.7 ml (350 mmoles) of triethylamine is added to the solution. Thereafter, the solution is cooled to approximately −15° C. with stirring and 44.1 ml (340 mmoles) of isobutylchloroformate is added dropwise. Stirring is continued at −15° C. After approximately 5 minutes a solution of 60.9 g (350 mmoles) of β-chloroalanine methyl ester hydrochloride in 350 ml of dimethylformamide is added dropwise to the reaction mixture over a period of 20 minutes while the temperature is maintained in the range of −15° to 20° C. Thereafter, a second equivalent of triethylamine (48.7 ml=350 mmoles) is added dropwise over 20 minutes while the temperature is maintained at −15° C. or below. The reaction mixture is stirred at −15° C. for 1 hour and then allowed to warm to 0° C. over the next hour. The mixture is filtered and the solids collected and washed with tetrahydrofuran (2×100 ml). The filtrate and washings are combined and evaporated under reduced pressure to afford tert-butoxycarbonyl-L-leucyl β-chloroalanine methyl ester as an oil.

The above obtained crude oil is dissolved in 700 ml of ethyl acetate and 49 ml (352 mmoles) of triethylamine is added to the solution with stirring. The reaction mixture is stirred at room temperature for 1 hour, then filtered and the collected solid material washed with ethyl acetate (2×100 ml). The combined filtrate and washings are then extraced with 1 M $NaHCO_3$ (3×200 ml), 1 M citric acid (2×200 ml) and water until the aqueous layer gives a pH indication greater than 4. The organic layer is separated and dried over magnesium sulfate with stirring for 3–5 hours at room temperature. Thereafter the resulting suspension is filtered and the collected solid material washed with ethyl acetate (2×100 ml). The combined filtrate and washings are evaporated under reduced pressure at 30° C. to afford an oily residue. To the resulting oil is added 200 ml of petroleum ether and evaporation is again effected under reduced pressure at 30° C. to afford a semisolid mass. The solid is triturated with 200 ml of petroleum ether and the resulting suspension is then refrigerated. After overnight refrigeration the suspension is filtered and the collected solid material washed with petroleum ether (3×100 ml) at 40° C., and then dried under vacuum over $P_2O_5$. The residue is characterized using thin-layer chromatography on silica gel developed with $CHCl_3/CH_3OH/CH_3COOH$ (10:2:1). The product, t-butyloxycarbonyl-L-leucyl-dehydroalanine methyl ester, obtained in 64% yield (i.e., 71 g) exhibits an Rf of 0.9.

The above obtained tert-butyloxcarbonyl-L-leucyl-dehydroalanine methyl ester (71 g), is dissolved in 450 ml of methanol and the resulting solution, protected from light by suitable means, is cooled in an ice bath. When the temperature of the solution reaches approximately 5° C., 123 ml (246 mmoles) of 2 N NaOH is added dropwise over a period of 20 to 30 minutes with vigorous stirring. The ice bath is then removed and stirring is continued for 40 minutes to 1 hour. The resulting reaction mixture is evaporated under reduced pressure at 30° C. until essentially all the methanol is removed. The aqueous solution is then diluted with 225 ml of water and 300 ml of chloroform and 63 g of citric acid are added with vigorous stirring. The clear biphasic mixture is separated, the aqueous layer is extracted with chloroform (2×100 ml) and the chloroform extracts are then combined and washed with 1 M NaCl (3×200 ml). Thereafter, the organic layer is separated and refrigerated in the presence of anhydrous magnesium sulfate. After overnight refrigeration the mixture is allowed to warm to room temperature and then filtered. The collected solid material is washed with chloroform (2×100 ml) and the combined filtrate and washings are then evaporated under reduced pressure at 30° C. The resulting residue is triturated with 200 ml of petroleum ether. The solid material is collected by filtration, washed with petroleum ether (2×100 ml) and then dried under vacuum. The crude product is dissolved in 300 ml of chloroform and insoluble impurities are removed by filtration. The chloroform solution, is diluted with petroleum ether while stirring until the first permanent tubridity occurs and is then referigerated at 4° C. After approximately 3 days, 27.9 g of needlelike crystals are collected and dried under vacuum over $P_2O_5$. An additional 3.6 g of material is obtained from the mother liquor upon dilution with 200 ml petroleum ether and refrigeration for an additional 24 hours at 4° C. The crystalline material is characterized using thin-layer chromatography on silica gel developed with CHCl$_3$/CH$_3$OH/CH$_3$COOH (10:2:1). The product, tert-butyloxycarbonyl-L-leucyl-dehydroalanine, obtained in 47% yield exhibits an Rf of 0.65; m.p. 154°–8° C. (dec.).

The above obtained tert-butyloxycarbonyl-L-leucyl-dehydroalanine (31.2 g) and 50 ml of trifluoroacetic acid are stirred at room temperature under anhydrous conditions in the absence of direct light. After approximately 30 minutes a solution is obtained and the evolution of CO$_2$ subsides. The reaction mixture is then evaporated under reduced pressure at 30° C. to afford an oily residue. The oil is triturated with 400 ml of a dry 50:50 ether/petroleum ether mixture until a solid begins to form. Anhydrous conditions are then maintained and vigorous stirring is carried out for approximately 5 minutes or until a colorless powdery solid material is obtained. The solid is collected, washed with a 50:50 ether/petroleum ether mixture (3×100 ml) and dried under high vacuum to afford the trifluoroacetate salt of leucyl dehydroalanine.

The above obtained salt (33 g, 105 mmoles) is dissolved in 400 ml of 0.1 M acetic acid containing 0.01% hydroquinone. It should be noted at this point that the foregoing operation, as well as all subsequent operations are performed in an area protected from overhead lighting or in suitably shielded glassware.

A resin bed of 400 ml AG1×2 resin (200–400 mesh) in the acetate form is prepared in a 600 ml coarse frit sintered glass funnel. The resin is then equilibrated with 0.1 M acetic acid containing 0.01% hydroquinone. Following equilibration, the solution prepared in the previous paragraph is applied to the resin bed. Fractions of 200 ml are then collected while washing the resin with approximately 1 liter of 0.1 M acetic acid containing 0.01 M hydroquinone. The fractions containing product are located by spotting samples on filter paper and spraying with ninhydrin reagent. The product is concentrated in the void volume with little or no trailing. The appropriate fractions are then pooled and lyophilized to afford 20.6 g of leucyl dehydroalanine.

EXAMPLE II

Repeating the procedures recited in Example I using other appropriate starting materials of formula (A), i.e., tert-butyloxycarbonyl glycine, tert-butyloxycarbonyl-L-alanine, tert-butyloxycarbonyl-glycly-L-proline, bis-tert-butyloxycarbonyl-L-lysyl-L-alanine and tert-butyloxycarbonyl-S-benzyl-L-cysteine is productive of glycyl dehydroalanine, alanyl dehydroalanine, glycyl-L-prolyl-dehydroalanine, lysyl-L-alanyl-dehydroalanine and S-benzyl-L-cysteinyl-dehydroalanine respectively.

EXAMPLE III

Serum samples are assayed for renal dipeptidase using the reagent system and method described below.

REAGENT SYSTEM

The following ingredients are combined in the specified amounts and ball-milled until homogeneous:

| | |
|---|---|
| glycyl dehydroalanine | 450 mg |
| lactate dehydrogenase | 3,600 I.U. |
| zinc acetate | 11 mg |
| N-tris (hydroxymethyl)methyl-2-aminoethanesulfonic acid | 766 mg |
| tris-(hydroxymethyl)-aminomethane | 200 mg |

Preparation of sufficient reagent for five assays comprises adding 2.1 mg of NADH to 7.4 mg of the above prepared homogeneous mixture followed by 15.5 ml of distilled water. The reagent system is then gently mixed by inversion to effect solution of the specific components.

METHOD

Assay of an individual serum sample is accomplished as follows:

Three milliliters of the reagent system is dispensed into a clean, dry cuvette having a 1 cm lightpath. All measurements are made at 340 nm using water as a blank. The cuvette containing the reagent system is placed in a constant temperature (30° C.) waterbath to bring the reagent to the the established temperature. The serum sample is also preincubated at 30° C. One hundred microliters (100 μl) of sample is added is added to the cuvette and gentle mixing is effected by inversion with a square of Parafilm over the open end. After mixing, the cuvette is immediately placed in a constant temperature (30° C.) cell compartment in a photometer capable of reading absorbance changes at 340 nm and calibrated for theoretical response to the molar absorbance of NAD. The initial absorbance ($A_o$) is read approximately 30 seconds after placing the cuvette in the instrument. Exactly 5 minutes after the initial reading, the final absorbance ($A_1$) is determined. When the absorbance change of the sample is greater than 0.1/minute, the test is repeated using less sample.

CALCULATIONS

Renal dipeptidase activity in mU/ml (International milliunits per milliliter) is calculated as follows:

$$mU/ml = \Delta A/min \times 4983$$

where $\Delta A/min$ is the observed change in absorbance in a one minute period, i.e., $$\Delta A/min = (A_o - A_1/5)$$

and 4983 is the conversion factor whose derivation is described infra.

In the event the 100 μl sample is too active or, not active enough, less sample or more sample, is used and a new conversion factor is employed as follows:

| Sample Volume | Conversion Factor |
|---|---|
| 50 μl | 9807 |
| 200 μl | 2572 |

DERIVATION OF THE FACTOR

Derivation of the conversion factor is based on the definition of International Units (U) as recommended by the International Union of Pure and Applied Chemistry and International Union of Biochemistry.

An International Unit is defined as the amount of enzyme which converts one micromole of substrate in 1 minute under standard conditions. The following formula derives the factor for calculating activity in mu/ml of sample:

$$\frac{mU \text{ renal peptidase}}{ml \text{ of sample}} = \frac{\Delta A/min \times T.V. \times 1000}{mM \text{ absorptivity} \times S.V. \times P}$$

where ΔA/min=observed absorbance change; mM absorptivity=6.22 at 340 nm for NAD; P=lightpath (cm); S.V.=sample volume (ml); T.V.=total assay volume (ml) and 1000=factor to convert IU to mU.

Accordingly, the calculation for renal dipeptidase activity using 3 ml of reagent and 100 μl of sample becomes:

$$mU/ml = \frac{\Delta A/min \times 3.1 \times 1000}{6.22 \times 0.1 \times 1} = A/min \times 4983$$

EXAMPLE IV

Serum samples are assayed for leucine aminopeptidase using the reagent system described below:

REAGENT SYSTEM

The following ingredients are combined in the specified amounts and ball-milled until homogeneous:

| | |
|---|---|
| L-leucyl-dehydroalanine | 2.5 g |
| lactate dehydrogenase | 10,400 I.U. |
| magnesium sulfate | 1.24 g |
| sucrose | 3.0 g |
| N-tris-(hydroxymethyl)methyl-2-aminoethane sulfonic acid | 6.88 g |
| tris-(hydroxymethyl)aminomethane | 2.32 g |

Preparation of sufficient reagent for five assays comprises adding 2.1 mg of NADH to 747.4 mg of the above prepared homogeneous mixture followed by 15.5 ml of distilled water. The reagent system is then gently mixed by inversion to effect solution of the specific components.

METHOD

Assay of individual serum samples is accomplished as set forth in Example III.

What is claimed is:

1. A reagent system for assaying a biological specimen for a peptidase enzyme, said reagent system comprising:
   (a) a peptide substrate in which the C-terminal amino acid is dehydroalanine;
   (b) the enzyme lactate dehydroagenase;
   (c) the reduced coenzyme NADH; and
   (d) a buffer material;
wherein (a), (b), (c) and (d) are present in amounts sufficient to ensure that the peptidase catalyzed hydrolysis of substrate is rate limiting.

2. The reagent system of claim 1 wherein the peptidase enzyme is renal dipeptidase and the substrate is glycyl-dehydroalanine.

3. The reagent system of claim 1 wherein the peptidase enzyme is renal dipeptidase and the substrate is L-alanyl-dehydroalanine.

4. The reagent system of claim 1 wherein the peptidase enzyme is leucine aminopeptidase and the substrate is L-leucyl-dehydroalanine.

5. The reagent system of claim 1 wherein the peptidase enzyme is dipeptidyl aminopeptidase II and the substrate is L-lysyl-L-alanyl-dehydroalanine.

6. The reagent system of claim 1 wherein the peptidase enzyme is dipeptidyl aminopeptidase IV and the substrate is glycyl-L-prolyl-dehydroalanine.

7. The reagent system of claim 1 wherein the peptidase enzyme is cystine aminopeptidase and the substrate is S-benzyl-L-cysteinyl-dehydroalanine.

8. A method of assaying a biological specimen for a peptidase enzyme using a reagent system comprising:
   (a) a peptide substrate in which the C-terminal amino acid is dehydroalanine;
   (b) the enzyme lactate dehydrogenase;
   (c) the reduced coenzyme NADH; and
   (d) a buffer material;
wherein (a), (b), (c) and (d) are present in amounts sufficient to ensure that the peptidase catalyzed hydrolysis of substrate is rate limiting; which method comprises:
   dissolving the reagent system in water to obtain a liquid reagent;
   mixing the liquid reagent with the specimen whereby the substrate is cleaved to produce pyruvic acid which oxidizes NADH to NAD; and
   determing the concentration of NAD with time.

9. A method according to claim 8 wherein the peptidase enzyme is renal dipeptidase and the substrate is glycyl-dehydroalanine.

10. A method according to claim 8 wherein the peptidase enzyme is renal dipeptidase and the substrate is L-alanyl-dehydroalanine.

11. A method according to claim 8 wherein the peptidase enzyme is leucine aminopeptidase and the substrate is L-leucyl-dehydroalanine.

12. A method according to claim 8 wherein the peptidase enzyme is dipeptidyl aminopeptidase II and the substrate is L-lysyl-L-alanyl-dehydroalanine.

13. A method according to claim 8 wherein the peptidase enzyme is dipeptidyl aminopeptidase IV and the substrate is glycyl-L-prolyl-dehydroalanine.

14. A method according to claim 8 wherein the peptidase enzyme is cystine aminopeptidase and the substrate is S-benzyl-L-cysteinyl-dehydroalanine.

* * * * *